United States Patent [19]

Brennan et al.

[11] 4,387,235
[45] Jun. 7, 1983

[54] INTERMEDIATES FOR THE PREPARATION OF GAMMA-PYRONES

[75] Inventors: Thomas M. Brennan, Old Lyme; Daniel P. Brannegan, Pawcatuck; Paul D. Weeks; Donald E. Kuhla, both of Gales Ferry, all of Conn.

[73] Assignee: Pfizer Inc., New York, N.Y.

[21] Appl. No.: 311,252

[22] Filed: Oct. 14, 1981

Related U.S. Application Data

[60] Division of Ser. No. 72,057, Sep. 4, 1979, Pat. No. 4,323,506, which is a division of Ser. No. 971,897, Dec. 21, 1978, abandoned, which is a division of Ser. No. 869,493, Jan. 16, 1978, Pat. No. 4,147,705, which is a division of Ser. No. 721,885, Sep. 9, 1976, Pat. No. 4,082,717, which is a continuation-in-part of Ser. No. 710,901, Aug. 2, 1976, abandoned.

[51] Int. Cl.$^3$ .......................................... C07D 309/22
[52] U.S. Cl. .................................................. 549/417
[58] Field of Search ........................................ 549/417

[56] References Cited

U.S. PATENT DOCUMENTS 3,707,482 12/1972 Laliberte ........................ 260/345.8
3,751,434 8/1973 Lefebvre ........................ 260/345.9
4,173,572 11/1979 Brennan et al. ..................... 549/417

OTHER PUBLICATIONS

Schenck et al., J. Am. Chem. Soc. 67, 2276 (1945).
Spielman et al., J. Am. Chem. Soc., 69, 2908 (1947).
Chawla et al., J. Org. Chem., 39, 3281 (1974).
Lichtenthaler et al., Angew Chem. Int. Ed., 8, 978 (1969).
Torii et al., Chemistry Letters No. 5, 495 (1976).
Hajivarnava, Carb. Res. 49, 93 (1976).
Paulsen et al., Tetrahedron Letters, No. 2, 133 (1972).

*Primary Examiner*—Nicky Chan
*Attorney, Agent, or Firm*—Connolly and Hutz

[57] ABSTRACT

2-methyl-3-hydroxy-4H-pyran-4-one is prepared by contacting 1(2-furyl)-1-ethanol in aqueous solution with two equivalents of a halogen oxidant at room temperature and then heating until the hydrolysis of the formed 4-halo-dihydropyran intermediate is substantially complete. Other valuable related gammapyrones are prepared in analogous manner from appropriate alcohols.

10 Claims, No Drawings

INTERMEDIATES FOR THE PREPARATION OF GAMMA-PYRONES

CROSS-REFERENCE TO RELATED APPLICATIONS

This application is a division of application Ser. No. 072,057 filed Sept. 4, 1979, now U.S. Pat. No. 4,323,506 which is a division of application Ser. No. 971,897 filed Dec. 21, 1978 and now abandoned, which is a division of application Ser. No. 869,493 filed Jan. 16, 1978 and now U.S. Pat. No. 4,147,705 which is a division of application Ser. No. 721,885 filed Sept. 9, 1976 and now U.S. Pat. No. 4,082,717 which is a continuation-in-part of application Ser. No. 710,901 filed Aug. 2, 1976 and now abandoned.

BACKGROUND OF THE INVENTION

Maltol is a naturally occurring substance found in the bark of young larch trees, pine needles and chicory. Early commercial production was from the destructive distillation of wood. Synthesis of maltol from 3-hydroxy-2-(1-piperidylmethyl)-1,4-pyrone was reported by Spielman and Freifelder in J. Am. Chem. Soc., 69, 2908 (1947). Schenck and Spielman, J. Am. Chem. Soc., 67, 2276 (1945), obtained maltol by alkaline hydrolysis of streptomycin salts. Chawla and McGonigal, J. Org. Chem. 39, 3281 (1974) and Lichtenthaler and Heidel, Angew. Chem., 81, 998 (1969), reported the synthesis of maltol from protected carbohydrate derivatives. Shono and Matsumura, Tetrahedron Letters No. 17, 1363 (1976), described a five step synthesis of maltol starting with methyl furfuryl alcohol.

The isolation of 6-methyl-2-ethyl-3-hydroxy-4H-pyran-4-one as one of the characteristic sweet-aroma components in refinery final molasses was reported by Hiroshi Ito in Agr. Biol. Chem., 40 (5), 827–832 (1976). This compound was previously synthesized by the process described in U.S. Pat. No. 3,468,915.

Syntheses of gamma-pyrones such as pyromeconic acid, maltol, ethyl maltol and other 2-substituted-3-hydroxy-gamma-pyrones are described in U.S. Pat. Nos. 3,130,204; 3,133,089; 3,140,239; 3,159,652; 3,365,469; 3,376,317; 3,468,915; 3,440,183; and 3,446,629.

Maltol and ethyl maltol enhance the flavor and aroma of a variety of food products. In addition, these materials are used as ingredients in perfumes and essences. The 2-alkenylpyromeconic acids reported in U.S. Pat. No. 3,644,635 and the 2-arylmethylpyromeconic acids described in U.S. Pat. No. 3,365,469 inhibit the growth of bacteri and fungi and are useful as flavor and aroma enhancers in foods and beverages and aroma enhancers in perfumes.

SUMMARY OF THE INVENTION

This invention is concerned with a process for perparing a gamma-pyrone of the formula

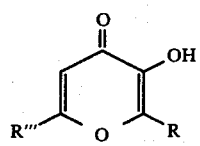

wherein R is hydrogen, alkyl of 1 to 4 carbon atoms, phenyl or benzyl; and R''' is hydrogen or alkyl of 1 to 4 carbon atoms which comprises contacting a furfuryl alcohol of the formula

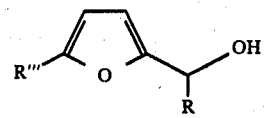

with two equivalents of a halogen oxidant and heating until the hydrolysis of the formed 4-halo-dihydropyran is substantially complete.

DETAILED DESCRIPTION OF THE INVENTION

The present invention is concerned with a novel and facile synthesis of maltol (2-methyl-3-hydroxy-4H-pyran-4-one) and related compounds.

A furfuryl alcohol in aqueous medium is treated with two equivalents of oxidant and the reaction mixture then heated to hydrolyze the final formed intermediate. The one pot process is represented as follows:

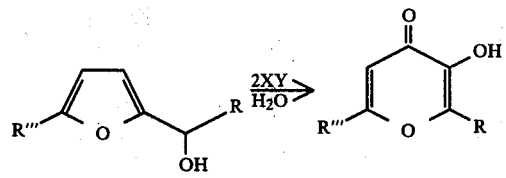

wherein R is hydrogen, alkyl of 1 to 4 carbon atoms, phenyl or benzyl; R''' is hydrogen or alkyl of 1 to 4 carbon atoms; and XY is $Cl_2$, $Br_2$, BrCl, HOCl, HOBr or mixtures thereof.

The reaction pathway is shown in the following scheme:

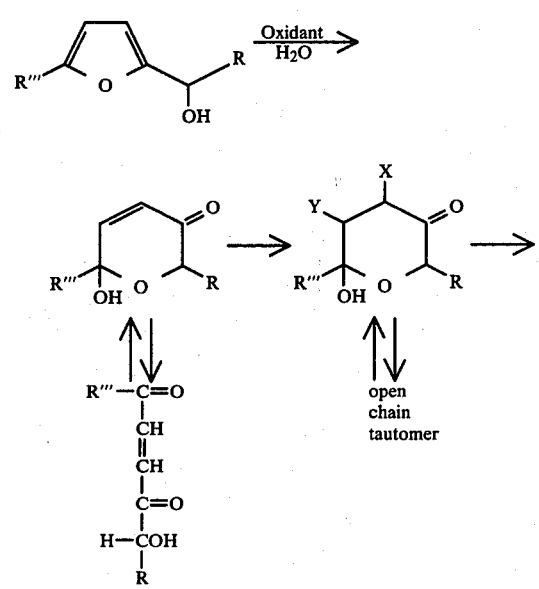

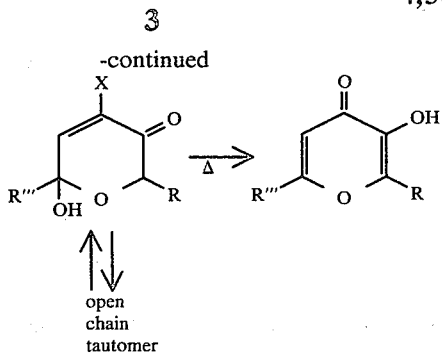

open chain tautomer

Lefebvre and co-workers in J. Med. Chem., 16, 1084 (1973) demonstrated that furfuryl alcohols could be directly converted to 6-hydroxy-2H-pyran-3(6H)-ones when a peracid oxidant such as peracetic acid or m-chloroperbenzoic acid is employed. The first step of the Lefebvre work uses a peracid in an organic solvent and probably leads to a 6-acetoxy or 6-m-chlorobenzoyloxy pyran derivative which is hydrolyzed to the 6-hydroxy compound during the aqueous work-up. Water is not used in the first step of the reaction, and would in fact be deleterious. In any case, the process of Lefebvre and co-workers cannot lead directly to the conversion of a furfuryl alcohol to a gamma-pyrone.

Critical to the process of the present invention is the use of an aqueous solution of a halogen oxidant. A furfuryl alcohol can be cleanly oxidized to a 6-hydroxy-2H-pyran-3(6H)-one using one equivalent of a halogen oxidant in water or water/organic co-solvent. It is surprising and an unexpected finding that 6-hydroxy-2H-pyran-3(6H)-ones can be converted to gamma-pyrones. A 6-hydroxy-2H-pyran-3(6H)-one may be regarded as a hemi-acetal of an aldehyde and as such might be expected to undergo numerous undesired side reactions such as over oxidation, aldol-type condensations, etc. Employing two equivalents of halogen oxidant in water or water and organic co-solvent, the reaction proceeds smoothly from a furfuryl alcohol to a gamma-pyrone. This novel one pot process offers the advantages of employing low cost $Cl_2$, $Br_2$, ClBr, HOCl, HOBr or mixtures thereof as the halogen oxidant. Isolation of the desired gamma-pyrone is greatly simplified since solvent, oxidant and by-product mineral acid are all volatile and can be removed in vacuo to afford crude gamma-pyrone directly in high yield by simple concentration.

The one pot process is operated by dissolving a furfuryl alcohol in water or water and a co-solvent. The co-solvent can be water miscible or water immiscible and can be selected from a wide range of solvents such as $C_1$ to $C_4$ alkanols or diols; $C_2$ to $C_{10}$ ethers; low molecular weight nitriles; and low molecular weight esters. The preferred co-solvents are $C_1$ to $C_4$ alkanols and $C_2$ to $C_{10}$ ethers, with methanol the choice of solvents because of cost. The solution is kept at a temperature of $-50°$ to $50°$ C., preferably $-10°$ to $10°$ C. To this solution is charged a desired furfuryl alcohol while simultaneously adding a halogen oxidant (two equivalents) to the reaction mixture. The temperature of the reaction mixture is maintained at $-10°$ to $10°$ C. during halogen addition. If a low-boiling co-solvent is employed, it is removed by distillation after all additions are complete. The reaction mixture is then heated to a temperature at which the hydrolysis proceeds at a reasonable rate (70° to 160° C.). The generally employed reaction temperature is 100°–110° C. The heating is continued until the hydrolysis of the formed 4-halo-dihyropyran intermediate is substantially complete (1 to 2 hours). The acid necessary to catalyze this final hydrolysis is generated in situ by loss of acid from the intermediates formed during the course of the reaction. Additional acid can be added if desired.

The halogen oxidant can be chlorine, bromine, chlorine-bromine, hypochlorous or hypobromous acid or mixtures thereof. Bromine chloride is a commercially available gas. It can be prepared in situ by the addition of chlorine to a solution of sodium or potassium bromide or by the addition of bromine to a solution of sodium or potassium chloride. Hypochlorous and hypobromous acid can be conveniently generated in situ by the addition of aqueous acid (HCl, $H_2SO_4$, HBr, etc.) to a solution of the alkali or alkali earth metal hypohalite, e.g., NaOCl, KOCl or $Ca(OCl)_2$. The preferred halogen oxidants, based on cost factors, are chlorine and bromine chloride prepared in situ.

If desired, a 6-hydroxy-2H-pyran-3(6H)-one can be prepared by contacting the appropriate furfuryl alcohol with one equivalent of a halogen oxidant. The isolated product is readily converted to the desired gamma-pyrone by contacting it with an additional equivalent of a halogen oxidant and hydrolyzing the formed 4-halogeno-6-hydroxy-2H-pyran-3(6H)-one as previously described.

Alternatively, a furfuryl alcohol in aqueous solution with an optional cosolvent is contacted at $-10°$ to $10°$ C. with two equivalents of a halogen oxidant. After stirring at room temperature for about 30 minutes, the pH of the reaction mixture is adjusted to about 2 with a strong base and the reaction mixture is extracted with a solvent such as ethyl acetate. Removal of the solvent yields the 4-halogeno-6-hydroxy-2H-pyran-3(6H)-one which may be hydrolyzed to the desired gamma-pyrone. The 4-halo-dihydropyran may be dehydrated by heating under vacuum to yield the 6,6'-oxybis[4-halogeno-2H-pyran-3(6H)-one]. This dimer yields the desired gamma-pyrone on hydrolysis, with added acid if desired.

The subject gamma-pyrones can also be prepared by treatment with a halogen oxidant with a compound of the formula

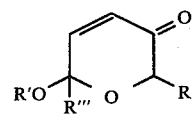

wherein R is hydrogen, alkyl of 1 to 4 carbon atoms, phenyl or benzyl and R' is alkyl of 1 to 4 carbon atoms and

wherein R" is methyl, ethyl or phenyl; and R''' is hydrogen or alkyl of 1 to 4 carbon atoms.

A 6-alkoxy-2H-pyran-3(6H)-one may be prepared by the method described in Tetrahedron Letters No. 17, 1363–1364 (1976). A furfuryl alcohol is anodically alkoxylated to the 2-(1-hydroxyalkyl)-2,5-dialkoxy-dihydrofuran. Treatment with a strong organic acid produces the desired 6-alkoxy compound. A 6-acyloxy compound may be prepared by conventional treatment of the 6-hydroxy compound with the appropriate anhydride in the presence of pyridine.

A 6-acyloxy or 6-alkoxy-2H-pyran-3(6H)-one is dissolved in a reaction-inert solvent selected from the group consisting of acetic acid, formic acid, trifluoroacetic acid, halogenated solvents, ethers, $C_1$ to $C_4$ alkanols or diols, low molecular weight ketones, nitriles, esters and amides. The preferred solvents are acetic acid, formic acid or methanol. An equivalent of a halogen oxidant such as chlorine, bromine, bromine chloride, hypochlorous acid or hypobromous acid is added at room temperature and the reaction mixture is heated to 70°–160° C., generally 100°–110° C., until the conversion to the desired gamma-pyrone is substantially complete (approximately 1–3 hours). The gamma-pyrone may be obtained from the cooled, neutralized reaction mixture on standing or by extracting the reaction mixture with a solvent such as chloroform which yields the gamma-pyrone on concentration.

With organic acids and other protic solvents such as formic acid, acetic acid, other organic acids and alkanols that have not been vigorously dried, no additional water is added in the above described reaction. However, with nonprotic solvents, water is necessary and is added for the conversion of the formed 4-halogeno-6-substituted-2H-pyran-3(6H)-one to the pyrone. When a low-boiling solvent is employed in the reaction, it is removed by distillation just before the reaction mixture is heated to 100°–110° C. for the hydrolytic conversion of the formed 4-halo-dihydropyran to the gamma-pyrone.

If desired, the 4-halo-dihydropyran may be prepared and isolated by conducting the halogenation at about −20° to 20° C., preferably 5°–10° C., in the presence of an organic base such as triethylamine. After about 30 minutes the reaction mixture is allowed to warm to room temperature, filtered to remove triethylamine hydrochloride and the solvent removed under vacuum to yield the 4-halo-dihydropyran. This compound is readily hydrolyzed to the gamma-pyrone by heating for about an hour in aqueous solution, with added acid if desired, at 70°–160° C., preferably 100°–110° C.

This process wherein the 6-acyloxy or 6-alkoxy-2H-pyran-3(6H)-one is contacted in an organic solvent with an equivalent of a halogen oxidant and the intermediate 4-halo-dihydropyran heated until the conversion to the desired gamma-pyrone is substantially complete differs from the multi-step process described by Shono and Matsumura in Tetrahedron Letters 17, 1363 (1976) wherein the 6-alkoxy-2H-pyran-3(6H)-one is treated with a methanolic solution of hydrogen peroxide with sodium hydroxide solution to yield an epoxy ketone. The isolated epoxy ketone is then refluxed in water with Dowex 50 ion exchange resin to yield the desired gamma-pyrone.

In the following examples where spectral data are given, NMR chemical shift data are reported by conventional literature symbolism and all shifts are expressed as δ units from tetramethyl silane:

s=singlet
d=doublet
t=triplet
q=quartet
m=multiplit
br=broad

EXAMPLE 1

In a 3-neck round bottom flask equipped with a magnetic stirring bar, a gas inlet tube, a thermometer and an addition funnel was added 20 ml of tetrahydrofuran and 50 ml of water. The solution was cooled to a temperature of 0° to 10° C. The addition funnel was charged with a solution of 1(2-furyl)-1-ethanol (0.089 moles) in 20 ml of tetrahydrofuran and this was added dropwise to the stirred reaction flask while chlorine (0.30 mole) was added via the gas inlet tube. The rate of addition was such that all the alcohol was added in the first 1.3–1.5 equivalents of chlorine (approximately 30 minutes) while maintaining the reaction temperature below 10° C. The reaction mixture was heated to reflux and the tetrahydrofuran removed by distillation. When the reaction mixture reached a temperature of about 105° C., a condenser was added and the refluxing continued for about 2 hours. The reaction mixture was then filtered hot, cooled, the pH adjusted to 2.2 and the reaction mixture was cooled to 5° C. Crystallization and filtration yielded 3.43 grams of crude 3-hydroxy-2-methyl-γ-pyrone (maltol). The aqueous filtrate was extracted with CHCl$_3$ to obtain a second crop of 2.58 g of maltol. Distillation of the combined solids and recrystallization from methanol gave 5.5 g (49%) of pure white maltol, m.p. 159.5°–160.5° C.

EXAMPLE 2

The method of Example 1 was repeated under varying conditions as shown in Table I with furfuryl alcohols of the formula

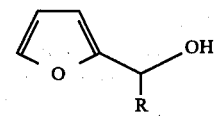

TABLE 1

| | One Pot Process using chlorine as the oxidant. | | | |
|---|---|---|---|---|
| R | Cosolvent | Temp. (°C.) of oxidation | Temp. (°C.) of hydrolysis | Yield (%) |
| CH$_3$ | methanol | 10 | 100 | 45 |
| CH$_3$ | methanol | 5 | 110 | 56 |
| CH$_3$ | methanol | −5 | 104 | 60 |
| CH$_3$ | methanol | −10 | 104 | 77 |
| CH$_3$ | methanol | −20 | 106 | 62–67 |
| CH$_3$ | THF | 10 | 105 | 49 |
| CH$_3$ | acetone | −5 | 110 | 36 |
| CH$_3$ | CH$_3$CN | −5 | 110 | 29 |
| CH$_3$ | Et OAc | 0 | 110 | 26 |
| CH$_3$ | none | 10 | 110 | 17–30 |
| CH$_3$ | benzene | 10 | 110 | 26 |
| CH$_3$ | methyl isobutyl ketone | 5 | 110 | 44 |
| CH$_3$ | isopropyl alcohol | 0 | 110 | 49 |
| CH$_2$CH$_3$ | methanol | 5 | 110 | 49 |
| CH$_2$CH$_3$ | methanol | −10 | 110 | 58 |
| CH$_2$CH$_3$ | THF | 10° | 110 | 47 |
| H | methanol | −10° | 110 | 57 |
| CH$_3$ | methanol | −30° | 110 | 50 |

THF = tetrahydrofuran
EtOAc = ethyl acetate

EXAMPLE 3

The method of Example 2 was repeated with comparable results employing each of the following co-solvents:
ethanol
n-propanol
iso-butanol
n-butanol
t-butanol
dioxane
ethyl ether
isopropyl ether
dimethoxy ethane
2-methoxy ethanol
2-ethoxy ethanol
ethylene glycol

EXAMPLE 4

In a 3-neck round bottom flask equipped with a stirring bar, a gas inlet tube and an addition funnel was added 20 ml of tetrahydrofuran, 50 ml of water and sodium bromide (0.20 mole). The solution was cooled to a temperature of 0° to 20° C. The addition funnel was charged with a solution of 1(2-furyl)-1-ethanol (0.18 mole) in 20 ml of tetrahydrofuran and this was added dropwise to the rapidly stirred reaction flask while gaseous chlorine (0.40 mole) is added via the gaseous inlet tube. The rate of the alcohol addition was such that a yellow orange color was maintained. The reaction temperature was kept below 20° C. with ice bath cooling. After the alcohol and chlorine had both been added to the reaction flask, the temperature was raised to reflux to distill off the tetrahydrofuran. The isolation procedure of Example 1 was used to isolate 12.47 g of pure maltol (55% yield).

Substantially the same results are obtained substituting potassium bromide for sodium bromide.

EXAMPLE 5

The method of Example 4 was repeated under varying conditions shown in Table 2 with furfuryl alcohols of the formula

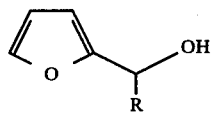

TABLE 2

One Pot Process using Cl—Br as the oxidant, generated by addition of chlorine in situ to NaBr.

| R | Cosolvent | Temp. (°C.) of oxidation | Temp. (°C.) of hydrolysis | Yield (%) |
|---|---|---|---|---|
| CH₃ | THF | 20° | 104 | 55 |
| CH₃ | THF | 27° | 110 | 54 |
| CH₃ | THF | 15° | 110 | 52 |
| CH₃ | Isopropyl ether | 25 | 110 | 46 |
| CH₃ | ethyl ether | 20 | 110 | 43 |
| CH₃ | acetone | 15 | 105 | 47 |
| CH₃ | CH₃OH | 15 | 110 | 32 |
| CH₂CH₃ | THF | 16 | 113 | 47 |
| H | THF | 20 | 109 | 48 |

THF = tetrahydrofuran

EXAMPLE 6

In a 3-neck round bottom flask equipped with a magnetic stirring bar, a gas inlet tube, a thermometer and an addition funnel was added 50 ml of tetrahydrofuran and 50 ml of water. This solution was then cooled to 0° C. and chlorine (0.10 mole) was added slowly to the reaction flask while 1(2-1-ethanol (0.09 mole) was added dropwise. The temperature of the reaction mixture was not allowed to exceed 10° C. Bromine (0.10 mole) was then added and the reaction mixture heated to reflux. Following the isolation procedure of Example 1, a yield of 5.7 g of maltol was obtained.

EXAMPLE 7

To a 4-neck round bottom flask equipped with a thermometer, a condensor and two addition funnels was charged 50 ml of tetrahydrofuran and 50 ml of water and the solution was cooled to 10° C. To this well stirred solution was added together in the two addition funnels bromine (0.20 mole) and 1(2-furyl)-1-ethanol (0.09 mole). The temperature of the reaction was maintained at 15° C. throughout the double addition. The reaction mixture was then heated to 75° C. for 10 hours. Maltol was isolated by the procedure of Example 1 (53% yield).

EXAMPLE 8

The method of Example 7 was repeated under varying conditions shown in Table 3 with furfuryl alcohols of the formula

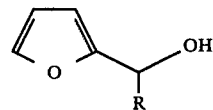

TABLE 3

| R | Cosolvent | Temp. (°C.) of oxidation | Temp. (°C.) of hydrolysis | Yield (%) |
|---|---|---|---|---|
| CH₃ | THF | 15° | 75 | 53 |
| CH₃ | CH₃OH | 5° | 105 | 47 |
| CH₃ | none | 15° | 100 | 30 |
| CH₂CH₃ | THF | 25 | 105 | 47 |
| H | THF | 15° | 100 | 45 |
| CH₃ | THF | 50° | 100 | 20 |

EXAMPLE 9

A 2.8 M sodium hypochlorite solution was prepared by passing chlorine gas (42.6 g) into a solution of 48 g of sodium hydroxide in 150 ml of water at 0° C. A solution of 1(2-furyl)-1-ethanol (0.05 mole) in 15 ml of tetrahydrofuran and 15 ml of water was prepared in a 3-neck flask and cooled to 5° C. While maintaining a pH from 1.0 to 0.8 with 6 N HCl, 21.7 ml of the hypochlorite solution was added dropwise to the reaction flask over a period of about 33 minutes while maintaining the reaction temperature below 5° C. A 15 ml portion of concentrated HCl was then added to the reaction mixture which was then heated to remove the tetrahydrofuran by distillation. Heating was continued for an additional hour. Maltol was isolated as described in Example 1.

Substantially the same results are obtained when sodium hypobromite is used in placed of sodium hypochlorite.

EXAMPLE 10

To a solution of 1(2-furyl)-1-ethanol (0.05 mole) in 15 ml of tetrahydrofuran and 15 ml of water at 5° C. is added 21.7 ml of 2.8 M sodium hypochlorite solution. Chlorine (0.05 mole) is added to the reaction flask via a gas inlet tube maintaining the reaction temperature below 5° C. The reaction mixture is then heated to reflux and the tetrahydrofuran removed by distillation. Heating is continued for an additional hour. The reaction mixture is cooled and maltol is isolated by the procedure described in Example 1.

EXAMPLE 11

To a 3-neck round bottom flask is charged a solution of 50 ml of water and 20 ml of tetrahydrofuran and the solution is cooled to 0° C. An addition funnel is charged with a solution of 1(2-furyl)-1-ethanol (0.89 mole) in 25 ml of tetrahydrofuran and this solution is added dropwise to the reaction flask while BrCl (0.30 mole) is added via a gas inlet tube. The rate of addition is such that all the furfuryl alcohol is added in the first 1.3–1.5 equivalents of BrCl while maintaining the temperature below 30° C. The reaction mixture is heated to reflux and the tetrahydrofuran removed by distillation. When the temperature reaches 105° C., a condensor is attached and the reaction mixture heated under reflux for about 2 hours. The reaction mixture is cooled and maltol isolated by the method of Example 1.

EXAMPLE 12

In a 3-neck round bottom flask equipped with a magnetic bar, a thermometer and two addition funnels is charged 25 ml of tetrahydrofuran and 50 ml of water. To this solution is added 1(2-furfyl)-1-ethanol (0.89 mole) in 25 ml of tetrahydrofuran while bromine (0.16 mole) is added dropwise while maintaining the temperature below 15° C. After the additions are complete, chlorine (0.10 mole) is added via a gas inlet tube and the reaction is heated to reflux. Maltol is isolated from the cooled solution by the method of Example 1.

EXAMPLE 13

6-hydroxy-2-methyl-2H-pyran-3(6H)-one

To a solution of 25 g of 1(2-furfyl)-1-ethanol in 125 ml of tetrahydrofuran and 125 ml of water at 5° C. was added 1 equivalent of bromine. The temperature was maintained at 5°–10° C. throughout the addition. The solution was adjusted to pH 2.1 and extracted with ethyl acetate (3×50 ml). The ethyl acetate extract was dried and evaporated to give a yellow oil. The oil was chromatographed on silica gel and eluted with chloroform-ethyl acetate (3:1) to give 4.8 g of clear oil which was shown by spectral data to be identical with 6-hydroxy-2-methyl-2H-pyran-3(6H)-one prepared from 6-methoxy-2-methyl-2H-pyran-3(6H)-one by acid hydrolysis [Tetrahedron 27, 1973 (1971)].

IR (CHCl₃) 3700, 3300, 1700 cm⁻¹.

NMR (CDCl₃, δ): 6.8-7.1 (1H, d of d); 6.0-6.2 (1H, d), 5.6 (1H, br. s, exchanges with D₂O); 5.4-5.5 (1H, d); 4.8-5.0 (1H, q); 1.3-1.6 (3H, t).

EXAMPLE 14

The method of Example 13 was repeated with a furfuryl alcohol of the formula

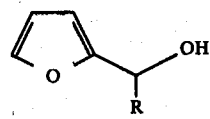

to yield a compound of the formula

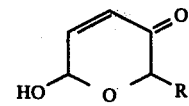

wherein R is hydrogen or ethyl.

Ethyl compound: IR (CHCl₃) 3600, 3340, 1706 cm⁻¹.

Hydrogen compound: IR (CHCl₃) 3565, 3300, 1703 cm⁻¹.

EXAMPLE 15

4-bromo-6-hydroxy-2-methyl-2H-pyran-3(6H)-one

To a solution of 25 g of 1(2-furyl)-1-ethanol in 125 ml of tetrahydrofuran and 125 ml of water at 0°–5° C. was added dropwise 2.2 equivalents of bromine. Throughout the addition the temperature was maintained at 5°–10° C. After the bromine addition the solution was stirred at room temperature for 30 minutes and the pH adjusted to 2.1 with 2 N NaOH solution. The reaction mixture was extracted with ethyl acetate (3×100 ml). The ethyl acetate extracts were combined, dried over MgSO₄, filtered and taken to dryness. The residue was chromatographed on silica gel and eluted with chloroform-ethyl acetate (95:5). The product was an orange oil which was rechromatographed on silica gel and eluted with chloroform-ethyl acetate (95:5).

NMR (CDCl, δ) 7.3 (1H, d); 5.6 (1H, d); 4.7-5.0 (1H, q); 1.1-1.5 (3H, m).

EXAMPLE 16

The method of Example 15 was repeated with a furfuryl alcohol of the formula

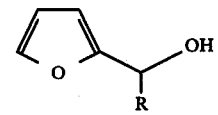

to yield a compound of the formula

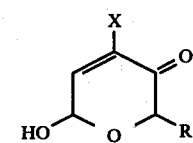

wherein R is hydrogen or ethyl.

Ethyl compound 4-bromo-6-hydroxy-2 ethyl 2H-pyran-3(6H)-one NMR (CDCl₃, δ) 7.4 (1H, d); 5.8 (1H, d); 4.6-4.9 (1H, m); 1.8-2.2 (2H, m); 1.0-1.3 (3H, t).

Hydrogen compound 4-bromo-6-hydroxy-2H-pyran-3(6H)-one NMR (CDCl₃, δ) 7.4 (1H, d); 5.5 (1H, d); 4.6 (2H, d of d).

EXAMPLE 17

A solution of 4-bromo-6-hydroxy-2-methyl-2H-pyran-3(6H)-one was prepared by dissolving the compound in either aqueous inorganic or organic acids. The solution was then heated to reflux, cooled to room temperature, the pH adjusted to 2.1 with 6 N NaOH and the reaction mixture extracted with chloroform. Concentration yielded maltol. The acids, time of reaction and yields of maltol were as follows:

| Acid | Concentration (%) | Reaction Time (Hrs.) | Yield (%) |
| --- | --- | --- | --- |
| HCl | 32 | 2 | 68 |
| HCl | 32 | 5 | 52 |
| HCl | 18 | 5 | 35 |
| HCl | 25 | 3 | 49 |
| HBr | 18 | 5 | 24 |
| $H_2SO_4$ | 35 | 2 | 26 |
| $H_3PO_4$ | 35 | 2 | 29 |
| $CH_3COOH$ | 35 | 2 | 69 |
| $CF_3COOH$ | neat | 3 | 36 |
| $HNO_3$ | 35 | 3 | 0.4 |
| $CF_3COOH$ | neat | 3 | 70 |
| $CH_3COOH$ | neat | 3 | 77 |
| HCOOH | neat | 3 | 24 |
| $H_2SO_4$ | 35 | 5 | 48 |

In addition, organic solvents such as benzene and toluene, together with acidic materials such as p-toluenesulfonic acid and Amberlite IR-120, may also be used.

EXAMPLE 18

The method of Example 15 was repeated employing chlorine in place of bromine and the appropriate furfuryl alcohols to produce the following compounds:

Methyl: 4-chloro-6-hydroxy-2-methyl-2H-pyran-3(6H)-one NMR (CDCl$_3$, δ): 7.1 (1H, d); 5.8 (1H, d); 4.6-5.0 (1H, m); 4.4 (1H, br. s); 1.2-1.5 (3H, m).

Ethyl: 4-chloro-6-hydroxy-2-ethyl-2H-pyran-3(6H)-one NMR (CDCl$_3$, δ): 7.0-7.1 (1H, d); 5.6-6.0 (2H, m), 4.4-5.0 (1H, m); 1.6-2.1 (2H, m); 0.9-1.1 (3H, t).

Hydrogen: 4-chloro-6-hydroxy-2H-pyran-3(6H)-one NMR (CDCl$_3$, δ): 7.1-7.2 (1H, d); 5.6 (1H, d); 4.4-4.9 (2H, d of d) (D$_2$O added).

EXAMPLE 19

The method of Example 15 may be repeated to yield a compound of the formula

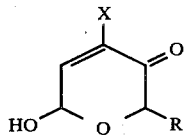

wherein R is propyl, butyl, phenyl or benzyl; X is bromine or chlorine.

EXAMPLE 20

4-Bromo-6-hydroxy-2-methyl-2H-pyran-3(6H)-one was heated under vacuum for 16 hours at 40° C. The resulting oily solid was crystallized from isopropyl alcohol to yield 6,6'-oxybis [4-bromo-2-methyl-2H-pyran-3(6H)-one], mp 125° C.

EXAMPLE 21

The method of Example 20 may be repeated with a compound of the formula

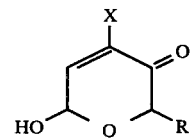

to yield a compound of the formula

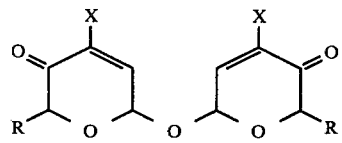

wherein R is hydrogen, ethyl, propyl, butyl, phenyl or benzyl; X is bromine or chlorine.

| R | X | M.P. (°C.) |
| --- | --- | --- |
| $CH_3$ | Cl | 177-179 |
| $CH_2CH_3$ | Cl | 132-135 |

EXAMPLE 22

A solution of 4-bromo-6-hydroxy-2-methyl-2H-pyran-3(6H)-one (0.0025 mole) in 20 ml of 35% phosphoric acid was refluxed for about 5 hours. Maltol (34%) was isolated by the method of Example 1.

EXAMPLE 23

A compound of the formula

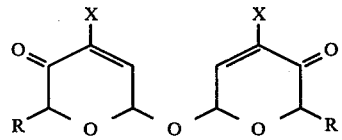

wherein R is hydrogen, methyl, ethyl, propyl, butyl, phenyl or benzyl and X is bromine or chlorine is treated by the method of Example 22 to yield a compound of the formula

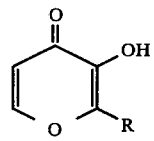

wherein R is as defined above.

EXAMPLE 24

A solution of 6-methoxy-2-methyl-2H-pyran-3(6H)-one (0.01 mole) in 20 ml of acetic acid was treated with gaseous chlorine (0.01 mole) at room temperature. The reaction mixture was then heated to reflux for about one hour, cooled to room temperature, diluted with 20 ml of water, the pH adjusted with 50% NaOH solution to 7.0 and the reaction mixture extracted with chloroform. The chloroform extract was concentrated to yield maltol which was recrystallized from methanol to give the pure product (56%), mp 159.5°–160.5° C.

EXAMPLE 25

The method of Example 24 may be repeated starting with a compound of the formula

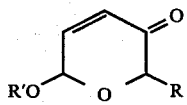

wherein R is hydrogen, alkyl of 2 to 4 carbon atoms, phenyl and benzyl; R' is alkyl of 2 to 4 carbon atoms and

where R" is methyl, ethyl or phenyl to yield a gamma-pyrone of the formula

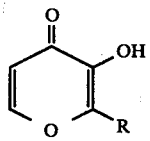

wherein R is hydrogen, alkyl of 2 to 4 carbon atoms, phenyl or benzyl.

EXAMPLE 26

The method of Example 24 may be repeated with comparable results replacing acetic acid with each of the following solvents:
formic acid
methanol
ethanol
tetrahydrofuran
benzene
ethylene glycol
trifluoroacetic acid
acetone
acetonitrile

EXAMPLE 27

The method of Example 24 may be repeated with comparable results replacing chlorine with bromine, sodium or potassium hypochlorite or hypobromite, gaseous bromine-chlorine or bromine-chlorine prepared in situ by the addition of chlorine to a solution containing sodium bromide or bromine to a solution of sodium chloride.

EXAMPLE 28

4-chloro-6-methoxy-2-methyl-2H-pyran-3(6H)-one

To a solution of 6-methoxy-2-methyl-2H-pyran-3(6H)-one (0.05 mole) in 70 ml of dichloromethane at −10° C. was added chlorine (0.05 mole) via a gas inlet tube. Following this addition, triethylamine (0.05 mole) was added slowly maintaining the temperature at −10° C. After 30 minutes of stirring the reaction mixture was allowed to warm to room temperature, filtered to remove triethylamine hydrochloride and the solvent removed under vacuum. Redissolving the crude product in ether-benzene and filtration removed the last traces of triethylamine hydrochloride. Removal of the solvent gave 4-chloro-6-methoxy-2-methyl-2H-3(6H)-one (yield, 99%). NMR analysis of the signals at 5.05 to 5.25 clearly showed two doublets in a 3 to 1 ratio corresponding to the proton at C-6 of the two possible isomers of the compound. Both optical forms of the trans isomer had been synthesized from a carbohydrate precursor by Paulsen, Eberstein and Koebernick, Tetrahedron Letters 4377 (1974).

EXAMPLE 29

4-bromo-6-methoxy-2-methyl-2H-pyran-3(6H)-one

The method of Example 28 was repeated replacing chlorine with bromine to obtain 4-bromo-6-methoxy-2-methyl-2H-pyran-3(6H)-one in 93% yield. The two optical forms of the trans isomer had been synthesized by Paulsen and co-workers, Tetrahedron Letters 4377 (1974).

EXAMPLE 30

The methods of Examples 28 and 29 may be repeated starting with a compound of the formula:

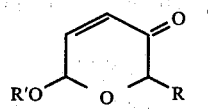

wherein R is hydrogen, alkyl of 2 to 4 carbon atoms, phenyl or benzyl; R' is alkyl of 2 to 4 carbon atoms to yield a compound of the formula

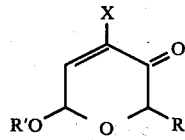

wherein R and R' are as defined above; and X is chlorine or bromine.

EXAMPLE 31

4-bromo-6-acetoxy-2H-pyran-3(6H)-one

A solution in dichloromethane of 6-acetoxy-2H-pyran-3(6H)-one, prepared by the method described in Tetrahedron 27, 1973 (1971), was brominated by the method of Example 6 to yield 4-bromo-6-acetoxy-2H-pyran-3(6H)-one, mp 78°–80° C. The mass spectrum of the compound showed the expected parent peaks at 234 and 236 mass units.

EXAMPLE 32

4-bromo-6-acetyl-2-methyl-2H-3(6H)-one

The method of Example 31 was repeated with 6-acetoxy-2-methyl-2H-pyran-3(6H)-one to yield 4-bromo-6-acetoxy-2-methyl-2H-3(6H)-one which showed parent masses of 249.96 and 247.96 by mass spectroscopy and the following MNR spectrum: ($\delta$, CDCl$_3$):7.3 (1H, d); 6.4 (1H, d of d); 4.7 (1H, Q); 2.2 (3H, S); 1.4 (3H, S).

EXAMPLE 33

The method of Example 28 may be repeated employing chlorine in place of bromine starting with a compound of the formula

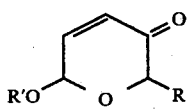

wherein R is hydrogen, alkyl of 1 to 4 carbon atoms, phenyl or benzyl; R' is alkyl of 1 to 4 carbon atoms and

where R' is methyl, ethyl or phenyl to yield a compound of the formula

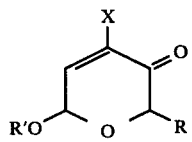

wherein R and R' are as defined above and X is chlorine.

EXAMPLE 34

To a round bottom flask equipped with a stirring bar and a condenser was added 4-chloro-6-methoxy-2-methyl-2H-pyran-3(6H)-one and acetic acid and the reaction mixture heated to reflux for an hour. Maltol (65%) was obtained on cooling.

EXAMPLE 35

The method of Example 34 was repeated with comparable results adding formic acid in place of acetic acid.

EXAMPLE 36

The method of Example 34 may be repeated starting with a compound of the formula

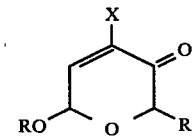

wherein R is hydrogen, alkyl of 1 to 4 carbon atoms, phenyl or benzyl; R' is alkyl of 1 to 4 carbon atoms and

where R'' is methyl, ethyl or phenyl; X is bromine or chlorine to yield a compound of the formula

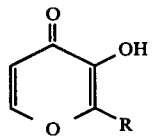

where R is hydrogen, alkyl of 1 to 4 carbon atoms, phenyl or benzyl.

EXAMPLE 37

6-methyl-2-ethyl-3-hydroxy-4H-pyran-4-one

In a three necked round bottom flask were combined 28 ml of methanol and 38 ml of water. The solution was cooled to −15° C. and 0.166 mole of 5-methyl-2-(2-hydroxy-propyl)furan (J. Org. Chem., 26, 1673, 1960) and 0.416 mole of chlorine were added simultaneously. During the addition, the reaction was maintained between −16° and −8° C. When addition was completed, the solution was warmed to 80° C. and refluxed for about 3 hours. Upon cooling to room temperature, the pH was adjusted to 2.1 and extracted with chloroform (3×100 ml). The combined organic layers were washed with water, brine and dried over magnesium sulfate. The organic solution was filtered and evaporated to give a thick dark solid. The solid was recrystallized twice from methanol to give 8.06 grams (30% yield) of white solid. Sublimation yielded pure product, m.p. 157°–159° C.

Analysis: Calc'd. for $C_8H_{10}O_3$: C, 62.33; H, 6.54. Found: C, 62.05; H, 6.44.

NMR (CDCl$_3$ δ); 6-CH$_3$, 2.33 (3H, s); 2-CH$_3$, 1.30 (3H, t); 2-CH$_2$-, 2.75 (2H, quartet); 5H, 6.23 (1H, s).

EXAMPLE 38

2,6-dimethyl-3-hydroxy-4H-pyran-4-one

In a three necked round bottom flask were combined 28 ml of water and 32 ml of methanol and cooled to −15° C. The solution was treated with 0.167 mole of 5-methyl-2-(α-hydroxy-ethyl)furan (J. Org. Chem., 26, 1673, 1960) and 0.416 mole of chlorine simultaneously. The temperature was maintained at −15° to −10° C. during addition. The reaction was allowed to warm to room temperature over 30 minutes and heated to reflux for 3 hours. The cooled solution was adjusted to pH 2.1 and extracted with chloroform (3×100 ml). The chloroform extracts were combined, washed with water and brine, dried over magnesium sulfate, filtered and evaporated. The residue, a dark oil, was chromatographed on silica gel developed with methylene chloride/ethyl acetate (95:5). The product, isolated by evaporation, was recrystallized from methanol as a tan solid (yield, 25%). Sublimation yielded white crystals, m.p. 161°–163° C.

Analysis: Calc'd. for $C_7H_8O_2$: C, 59.99; H, 5.75. Found: C, 59.83; H, 5.82.

NMR (CDCl$_3$, δ); 6-CH$_3$, 2.33 (3H, s); 2-CH$_3$, 2.26 (3H, s); 5-H, 6.10 (1H, s).

What is claimed is:

1. A compound of the formula

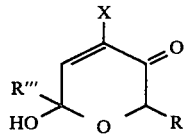

wherein R is hydrogen, alkyl of 1 to 4 carbon atoms, phenyl or benzyl; R''' is hydrogen or alkyl of 1 to 4 carbon atoms; and X is chlorine or bromine.

2. A compound of claim 1 wherein R''' is hydrogen.
3. A compound of claim 2 wherein X is chlorine.
4. The compound of claim 3 wherein R is methyl.
5. The compound of claim 3 wherein R is ethyl.
6. The compound of claim 3 wherein R is hydrogen.
7. A compound of claim 2 wherein X is bromine.
8. The compound of claim 7 wherein R is methyl.
9. The compound of claim 7 wherein R is ethyl.
10. The compound of claim 7 wherein R is hydrogen.

* * * * *